United States Patent [19]

Ogawa

[11] Patent Number: 6,160,087
[45] Date of Patent: Dec. 12, 2000

[54] PEPTIDES HAVING AN AMINO ACID SEQUENCE FROM THE FIMBRIAL PROTEIN OF PORPHYROMONAS GINGIVALIS AND THEIR USES

[75] Inventor: Tomohiko Ogawa, Toyonaka, Japan

[73] Assignees: Meito Sangyo Kabushiki Kaisha, Aichi; Kyowa Medex Co., Ltd.; Kyowa Hakko Kogyo Co, Ltd., both of Tokyo, all of Japan

[21] Appl. No.: 08/619,557

[22] PCT Filed: Sep. 28, 1994

[86] PCT No.: PCT/JP94/01589

§ 371 Date: Mar. 27, 1996

§ 102(e) Date: Mar. 27, 1996

[87] PCT Pub. No.: WO95/09181

PCT Pub. Date: Apr. 6, 1995

[30] Foreign Application Priority Data

Sep. 28, 1993 [JP] Japan .................................. 5-264140

[51] Int. Cl.[7] .......................... A61K 38/00; A61K 31/70; A61K 39/02; C07K 17/00
[52] U.S. Cl. ................... 530/300; 424/184.1; 424/234.1; 424/242.1; 424/185.1; 424/401; 514/44; 530/324; 530/325; 530/326; 530/327; 530/328; 530/329; 530/330
[58] Field of Search .............................. 424/184.1, 234.1, 424/242.1, 185.1, 401; 514/44; 530/300, 326, 324, 325, 330, 329, 328, 327

[56] References Cited

U.S. PATENT DOCUMENTS

| | | |
|---|---|---|
| 4,661,350 | 4/1987 | Tsurumizu et al. . |
| 4,689,221 | 8/1987 | Kiyoshige et al. ........................ 424/87 |
| 5,212,059 | 5/1993 | Schwartz et al. ........................... 435/6 |
| 5,310,542 | 5/1994 | Au et al. . |
| 5,334,503 | 8/1994 | Snyder et al. . |
| 5,348,733 | 9/1994 | Morishima et al. . |
| 5,432,055 | 7/1995 | Evans et al. . |
| 5,494,672 | 2/1996 | Hodges et al. . |
| 5,536,497 | 7/1996 | Evans et al. . |
| 5,830,710 | 11/1998 | Progulske-Fox et al. . |
| 5,948,636 | 9/1999 | Mori et al. . |
| 6,017,532 | 1/2000 | Travis et al. . |

FOREIGN PATENT DOCUMENTS

| | | |
|---|---|---|
| 0 239 776 | 10/1987 | European Pat. Off. . |
| 0 269 388 | 6/1988 | European Pat. Off. . |
| 0 439 212 A1 | 7/1991 | European Pat. Off. . |
| 0 439 214 A1 | 7/1991 | European Pat. Off. . |
| 4-229198 | 8/1982 | Japan . |
| 59-128338 | 7/1984 | Japan . |
| 61-140527 | 6/1986 | Japan . |
| 61-162753 | 7/1986 | Japan . |
| 61-277632 | 12/1986 | Japan . |
| 61-289024 | 12/1986 | Japan . |
| 62-417 | 1/1987 | Japan . |
| 1-144997 | 6/1989 | Japan . |
| 1-144998 | 6/1989 | Japan . |
| 1-313438 | 12/1989 | Japan . |
| 2-499 | 1/1990 | Japan . |
| 2-53458 | 2/1990 | Japan . |
| 2-53716 | 2/1990 | Japan . |
| 2-107969 | 4/1990 | Japan . |
| 2-107970 | 4/1990 | Japan . |
| 2-135096 | 5/1990 | Japan . |
| 2-218620 | 8/1990 | Japan . |
| 4-59736 | 2/1992 | Japan . |
| 4-59737 | 2/1992 | Japan . |
| 4-63865 | 2/1992 | Japan . |
| 4-355339 | 12/1992 | Japan . |
| 5-132428 | 5/1993 | Japan . |
| 60-142915 | 7/1995 | Japan . |

OTHER PUBLICATIONS

Dashper et al, Australian Dental Journal, 43/2:99–104, 1998.
Nakamura et al, FEMS Microbiol. Lett., 175:267–72, 1999.
Weinberg et al, Infection & Immunity, 65/1:313–316, 1997.
Choi et al, Infection & Immunity, 66/1:391–393, 1998.
Ogawa et al, FEMS Immunol & Med. Microbiol 11:247–56, 1995.
Deslauriers et al, Inf & Imm. 64(2):434–440, 1996.
Hamada et al, Inf & Imm. 64(11):4788–4794, 1996.
Nakayama et al, J. Bacteriol, 178(10):2818–2824, 1996.
Chandad et al, Inf & Imm. 63(12):4755–4763, 1995.
Amano et al, Inf & Imm. 62(8):3372–3380, 1994.
Ogawa et al, Vaccine, 15(2):230–36, 1997.
Nagata et al, Inf & Imm. 65(2):422–427, 1997.
Kawata et al, Inf & Imm. 65(2):815–817, 1997.
Weinberg et al, Inf & Imm. 65(1):313–316, 1997.
Lee et al, Inf & Imm., 59(1):383–389, 1991.
Ogawa et al, FEMS Microbiol Letters, 120:23–30, 1994.
Malek et al, J. Bacteriol, 176(4):1052–1059, 1994.
Evans et al Inf & Imm, 60(7):2926–2935, 1992.
Fujiwara et al, BBRC, 197(1):241–247, 1993.
Houghton et al, Vaccines 86 pp 21–25, 1986.
Bowie et al, Science, 247:1306–1310, 1990.
Bixler et al, Synthetic Vaccines vol. 1:39–71, 1987.
Muhammad et al, Pakistan Vet. J. 16(3):119–121, 1996.
Sharma et al, Appl. & Environ. Microbiol, 62(11):3933–38, 1996.

(List continued on next page.)

*Primary Examiner*—Nita Minnifield
*Attorney, Agent, or Firm*—Wenderoth, Lind & Ponack, L.L.P.

[57] ABSTRACT

There are provided peptides (each having 5 to 10 amino acid residues) corresponding to fragments derived from the amino acid sequence of the 41 kD sub-unit protein constituting the fimbriae of Porphyromonas gingivalis, or salts of the peptides. Further provided are compositions for diagnosis of periodontal disease containing them, vaccines for prophylaxis of periodontal disease containing part of them, and the oral compositions for prophylaxis or treatment of periodontal disease containing antibodies obtained by immunizing animals with the peptides.

Peptides are provided which are lowered in nonspecific reactivity and can be used more safely for the above compositions, compared to the above protein and peptides therefrom having 20 amino acid residues.

13 Claims, No Drawings

OTHER PUBLICATIONS

Klausen et al, Oral Microbiol. Immunol., 6:193–201, 1991.
Ogawa et al, Oral Microbiol. Immunol., 6:332–340, 1991.
Ogawa et al, Vaccine, 15/2: 230–236, 1997.
Sharma et al, Appl. & Environ. Microbiol 62/11:3933–3938, Nov. 1996.
Hamada et al Microbiol Immunol 38/12: 921–930, 1994.
Ogawa et al, J. Med. Microbiol 40:397–402, 1994.
Evans et al, In: Molecular Pathogenesis of pp267–278 Periodontal Disease. Editors Genco et al, 1994.
Ogawa, J. Med. Microbiol, 41:349–358, 1994.
Ogawa et al, Vaccine 15/15:1598–1605, 1997.
W.J. Loesche et al., "Bacterial Profiles of Subgingival Plaques in Periodontitis", J. Periodont, 56, 447–456, 1985.
M.A. Listgarten et al., "Positive correlation between the proportions of subgingival spirochetes and motile bacteria and susceptibility of human subjects to periodontal deterioration", J. Clin. Periodontol, 8, 122–138, 1981.
J.J. Zambon et al., "Immunological assays for putative periodontal pathogens", Oral Microbiol. Immunol. 1, 39–44, 1986.
W.J. Loesche et al., "The identification of bacteria associated with periodontal disease and dental caries by enzymatic methods", Oral Microbiol. Immunol. 1, 65–70, 1986.
C. Mouton et al., "Serum Antibodies to Oral *Bacteroides asaccharolyticus* (*Bacteroides gingivais*): Relationship to age and Periodontal Disease", Infection and Immunity, 31, 182–192, 1981.

T. Ogawa et al., "Bacteroides–specific IgG and IgA subclass antibody–secreting cells isolated from chronically inflamed gingival tissues", Clin. Exp. Immunol. 76, 103–110, 1989.

Ogawa et al., "Immunobiological activities of synthetic peptide segments of fimbrial protein from *Porphyromonas Gingivalis*", BBRC, 180, No. 3, 1335–1341, 1991.

Evans et al., "Immunization with fimbrial protein and peptide protects against *Porphyromonas Gingivalis*–induced periodontal tissue destruction", Adv. Exp. Med. Biol. 327, 255–262, 1992.

Lee et al. "Synthetic Peptides Analogous to the Fimbrillin Sequence Inhibit Adherence of *Porphyromonas gingivalis*", Infection and Immunity, vol. 60, No. 1, pp. 1662–1670, Apr. 1992.

Ogawa et al., "Hemagglutinating and Chemotactic Properties of Synthetic Peptide Segments of Fimbrial Protein from *Porphyromonas gingivalis*", Infection and Immunity, vol. 62, No. 8, pp. 3305–3310, Aug. 1994.

Dickinson et al., "Molecular Cloning and Sequencing of the Gene Encoding the Fimbrial Subunit Protein of *Bacteroides gingivalis*", Journal of Bacteriology, vol. 170, No. 4, pp. 1658–1665, Apr. 1988.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Glu Asn Ala Thr Lys Val Glu Asp Ile Lys
1               5                   10

(2) INFORMATION FOR SEQ ID NO:2:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Glu Val Lys Ala Leu Thr Thr Glu Leu Thr
1               5                   10

(2) INFORMATION FOR SEQ ID NO:3:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Ala Glu Asn Gln Glu Ala Ala Gly Leu Ile
1               5                   10

(2) INFORMATION FOR SEQ ID NO:4:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Ala Ala Gly Leu Ile Met Thr Ala Glu Pro
1               5                   10

(2) INFORMATION FOR SEQ ID NO:5:

(i) SEQUENCE CHARACTERISTICS:
       (A) LENGTH: 10 amino acids
       (B) TYPE: amino acid
       (C) STRANDEDNESS: single (D) TOPOLOGY:  linear (ii) MOLECULE TYPE: peptide (xi) SEQUENCE DESCRIPTION: SEQ ID NO:5:

Thr Gly Ser Leu Thr Thr Phe Asn Gly Ala
1               5                   10

(2) INFORMATION FOR SEQ ID NO:6:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE: peptide (xi) SEQUENCE DESCRIPTION: SEQ ID NO:6:

Thr Phe Asn Gly Ala Tyr Thr Pro Ala Asn
1               5                   10

(2) INFORMATION FOR SEQ ID NO:7:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE: peptide (xi) SEQUENCE DESCRIPTION: SEQ ID NO:7:

Gly Phe Tyr Val Leu Glu Asn Asp Tyr Ser
1               5                   10

(2) INFORMATION FOR SEQ ID NO:8:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE: peptide (xi) SEQUENCE DESCRIPTION: SEQ ID NO:8:

Ala Asn Gly Gly Thr Ile His Pro Thr Ile
1               5                   10

(2) INFORMATION FOR SEQ ID NO:9:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE: peptide (xi) SEQUENCE DESCRIPTION: SEQ ID NO:9:

Glu Gly Lys Thr Tyr Tyr Pro Val Leu Val
1               5                   10

(2) INFORMATION FOR SEQ ID NO:10:

(i) SEQUENCE CHARACTERISTICS:
         (A) LENGTH:  5 amino acids
         (B) TYPE:  amino acid

```
            (C) STRANDEDNESS:  single
            (D) TOPOLOGY:  linear (ii) MOLECULE TYPE: peptide (xi) SEQUENCE DESCRIPTION: SEQ ID NO:10:

Glu Asn Ala Thr Lys
1               5

(2) INFORMATION FOR SEQ ID NO:11:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:11:

Val Met Val Tyr Asn Gly Glu Gln Gln Glu
1               5                   10

(2) INFORMATION FOR SEQ ID NO:12:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:12:

Arg Thr Leu Val Val Met Ala Asn Thr Gly
1               5                   10

(2) INFORMATION FOR SEQ ID NO:13:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:13:

Asn His Ile Glu Asn Asp Pro Leu Lys Ile
1               5                   10

(2) INFORMATION FOR SEQ ID NO:14:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:14:

Asp Ala Asn Tyr Leu Thr Gly Ser Leu Thr
1               5                   10

(2) INFORMATION FOR SEQ ID NO:15:

(i) SEQUENCE CHARACTERISTICS:
            (A) LENGTH:  10 amino acids
```

```
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:15:

Trp Leu Ser Arg Asn Tyr Val Ala Pro Ala
1               5                   10

(2) INFORMATION FOR SEQ ID NO:16:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:16:

Leu Cys Val Tyr Gly Lys Leu Gln Lys Asn
1               5                   10
```

PEPTIDES HAVING AN AMINO ACID SEQUENCE FROM THE FIMBRIAL PROTEIN OF PORPHYROMONAS GINGIVALIS AND THEIR USES

This application is a 371 of PCT/JP94/01589 filed Sep. 28, 1994.

BACKGROUND OF THE INVENTION

1. Field of the Invention

The present invention relates to peptides corresponding to fragments derived from the amino acid sequence of the 41 kD subunit protein constituting the fimbriae of Porphyomonas gingivalis, and their uses. More specifically, the invention relates to peptides acting as antigens which antigen-antibody react with antibodies against the 41 kD subunit protein, and uses of the peptides for detection of specific antibodies, etc. in the serum, saliva and gingival crevice fluid of patients with periodontal disease, and for prophylactic agents and treating agents of periodontal disease.

2. Description of Related Art

Periodontal diseases are classified into gingivitis and periodontitis, and further, periodontitis includes adult periodontitis, localized juvenile periodontitis, etc., but actually, 90% or more of periodontitis is occupied by adult periodontitis. These periodontal diseases are diseases including inflammations of gingiva, bleeding, drainage, formation of periodontal pockets, destruction of periodontal membranes, absorption of alveolar bones, and lability or loss of teeth. Various bacteria exist at the lesions of these periodontal diseases, and among them, Porphyomonas gingivalis is considered to be a main periodontopathic organism, and remarkable increase of the bacterium is observed at the lesions of periodontal diseases particularly adult periodontitis.

At present, methods for treating periodontal disease are not perfectly established, and it is considered to be the most important to find periodontal disease as early as possible, grasp its pathologic states accurately, and make appropriate treatments, and further, prophylaxis of periodontal disease by development of vaccines for periodontal disease is desired.

First, as to diagnosis of periodontal disease, a diagnostic method for finding periodontal disease as early as possible and grasping its pathologic state accurately has been expected, but actually, reliable diagnostic drugs for periodontal disease has not yet been developed. However, if ventured to be mentioned, as a means for diagnosing periodontal disease through paying attention to periodontopathic organisms, there are various methods for knowing the presence or number of these periodontopathic organisms. Further, there have been proposed methods to assay a specific antibody against a periodontopathic organism and utilize the result for diagnosis of periodontal disease. Still further, methods have been proposed comprising assaying an inflammatory product in the gingival crevice fluid of a patient with periodontal disease.

There are various methods for knowing the presence or number of these periodontopathic organisms. For example, it was conducted to culture periodontopathic organisms in the dental plaques, gingival crevice fluid, saliva, etc. of a patient with periodontal disease in a blood agar medium under an anaerobic condition, and investigate detailed biochemical properties of the resultant various colonies, and thereby detect the periodontopathic organisms (Loesche, W. J., Syed, S. A., Schmidt, E. and Morrison, E. C.: *J. Periodont.* 56, 447–456, 1985, etc.).

There has been conducted Gram staining, under microscopic observation, of periodontopathic organisms in dental plaques, gingival crevice fluid, saliva, etc. of a patient with periodontal diseases, or there has been made an examination under a dark-field microscope (Listgarten, M. A. and Levin, S.: *J. Clin. Periodontol.* 8, 122–138, 1981, etc.). There has also been carried out the detection of a periodonto-pathic organism by combining an antibody against it with a fluorescent dye (Zambon, J. J., Bochacki, V. and Genco, R. J.: *Oral Microbiol. Immunol.* 1, 39–44, 1986).

Further, it has been conducted to detect periodontopathic organisms in the dental plaques, gingival crevice fluid, saliva, etc. of a patient with a periodontal disease, according to an immunological method such as enzyme-linked immunosorbent assay (ELISA method), using antibodies against the respective periodontopathic organisms (see, Zambon, J. J., Bochacki, V. and Genco, R. J.: *Oral Microbiol. Immunol.* 1, 39–44, 1986; Japanese Laid-open Patent Publication No. 159762/1988; ibid. 107970/1990; ibid. 212061/1992; ibid. 355339/1992; ibid. 10954/1993; and EP 239,776 A).

Further, it has been conducted to pay attention to enzymes produced by periodontopathic organisms, and detect the periodontopathic organisms in the dental plaques, gingival crevice fluid, saliva, etc. of a patient with periodontal disease, using their enzymatic activities as an index (see Loesche, W. J., *Oral Microbiol. Immunol.* 1, 65–70, 1986; Japanese Laid-open Patent Publication No. 144997/1989; ibid. 144998/1989; ibid. 499/1990; and ibid. 229198/1992).

Recently, it has also been conducted to pay attention to genes of periodontopathic organisms, and detect the periodontopathic organisms in the dental plaques, gingival crevice fluid, saliva, etc. of a patient with periodontal disease, using a DNA probe method (DMDx (trademark), Biotechnica Diagnostics Co.; and see Japanese Laid-open Patent Publication No. 135096/1990; and ibid. 502640/1991). Further, it is becoming possible to detect an extremely slight amount of cells, according to the PCR (polymerase chain reaction) method.

However, diagnostic methods, as above-mentioned, for periodontal disease to know the presence and number of periodontopathic organisms are usable only for diagnosis of pathogenesis, and are insufficient for grasping the pathologic state of a patient. As a diagnostic method which makes a pair therewith, and is for knowing the response of a patient as a host to periodontopathic organisms and thereby grasping the pathologic state of the patient, there can be thought a diagnostic method for periodontal disease to know a specific antibody against a periodontopathic organism, and further its class and subclass. A diagnostic method for periodontal disease to know the presence and number of periodontopathic organisms is also, of course, important, and it is said that it is important to conduct appropriate diagnosis of periodontal disease by combining both methods.

As one of such diagnostic methods, a method is proposed to assay the specific antibody titer against a periodontopathic organism of a patient with adult periodontitis by the ELISA method, and diagnose the periodontal disease of the patient from both of the results and the results of dental checkups (see Mouton, C., et al.: *Infection and Immunity* 31, 182–192, 1981; Japanese Laid-open Patent Publication No. 162753/1986; and ibid. 107969/1990).

Further, recently, a possibility that a diagnostic method for periodontal disease is effective based on not only increase of a specific antibody against a periodontopathic organism of a patient with periodontal disease, but the fact that the subclass of the specific antibody changes from $IgG_1$ to $IgG_4$ together with change of the pathologic state of the periodontal disease is proved by the ELISPOT method to detect antibody-producing cells against periodontopathic organisms in the gingiva tissue of a patient of adult periodontitis (T. Ogawa et al.: *Clin. exp. Immunol.* 76, 103–110, 1989).

When increase of a specific antibody against a periodontopathic organism of a patient with periodontal disease, and further change of its class or subclass are checked, an antigen used for detection becomes necessary. In the above usual methods, entire cells of a periodontopathic organism, or cell surface components such as lipopolysaccharides and fimbriae as an antigen have been used as antigens. However, it is difficult to obtain a large amount of pure antigen by the procedure of separation and purification, and many nonrelevant reactions take place thereon, and thus, they are not desirable for accurately checking increase of specific antibodies against the periodontopathic organisms of a patient with periodontal disease, and further their classes or subclasses.

*BBRC.* 180, No. 3, 1335–1341 (1991) reports the immunogenicity of a synthetic peptide composed of 20 amino acid residues in the 41 kD subunit protein molecule constituting the fimbriae of Porphyomonas gingivalis.

Further, it is disclosed in Japanese Laid-open Patent Publication No. 135096/1990 to use a component derived from a periodontopathic organism in a patient with periodontal disease for detecting a specific antibody against the periodontopathic organism, but the antigenic protein derived from Porphyomonas gingivalis disclosed therein utterly differs from the fimbria of Porphyomonas gingivalis as a substance, and further, is not desirable because it is troublesome to prepare an antigen as an entire protein. As one of other diagnostic methods for periodontal disease, there is a method to assay an inflammatory product. For example, a method is proposed to assay collagenase (Periocheck (trademark): Advanced Clinical Technologies, Westwood, Mass.), a cathepsin-like activity (Progno Stick: Dentsply Corp., York Pa.), or glucuronidase (Abbott Laboratories, North Chicago, Ill.). However, these methods have problems in specificity.

In Japanese Patent Publication No. 13205/1991, Japanese laid-open Patent Publication No. 140527/1986 and Japanese laid-open Patent Publication No. 132428/1993, it is proposed to use the fimbriae of Porphyomonas gingivalis as a prophylactic vaccine against periodontitis (or periodontal disease). However, there are many problems in using fimbriae separated and purified according to methods mentioned therein. Namely, when the fimbriae are used after separation and purification, it is thought that substances other than the fimbriae, for example, cellular components other than the fimbriae such as lipopolysaccharides which are pyrogens mingle therein, and the fimbriae are not desirable as vaccines. As understood from that it is shown in *BBRC.* 180, No. 3, 1335–1341 (1991) that these fimbriae themselves exhibit various biological activities, there is a possibility that use of whole of these fimbriae causes actions other than the action as a vaccine, for example, a prophlogistic action and a pyrogenic action, which is undesirable.

Incidentally, the antigenic protein derived from Porphyomonas gingivalis, which is exhibited to be used as a vaccine in Japanese Patent Publication No. 135096/1990, differs from the peptide of the fimbriae of Porphyomonas gingivalis in the invention in amino acid sequence, and it is not desirable to use the entire antigenic protein because preparation of the vaccine is troublesome and there is a possibility that it causes actions other than the action as a vaccine, for example, a prophlogistic action and a pyrogenic action. Further, the synthetic peptide of the fimbriae of Porphyomonas gingivalis shown in *Adv. Exp. Med. Biol.* 327, 255–262, 1992 differs from the peptide of the fimbriae of Porphyomonas gingivalis in the invention in region, and it is not desirable, as in the above case, to use the entire protein because preparation of the vaccine is troublesome and there is a possibility that it causes actions other than the action as a vaccine, for example, a prophlogistic action and a pyrogenic action.

An oral cavity composition containing an antibody obtained by immunization with the whole cell or fimbrial protein of Porphyomonas gingivalis is proposed in Japanese laid-open Patent Publication No. 142915/1985, ibid. 277632/1986, ibid. 289024/1986, ibid. 417/1987, ibid. 313438/1989, ibid. 53458/1990, ibid. 53716/1990, ibid. 218620/1990, ibid. 59736/1992, ibid. 59737/1992 and Japanese Patent Publication No. 63865/1992. However, antibodies against the whole cell or fimbrial protein prepared by these methods possibly cause cross reaction with substances other than the desired antigen, and are not desirable for the present objects.

Thus, the object of the invention lies in providing peptides capable of effective detection of increase of specific antibodies against periodontopathic organisms in the patient with periodontal disease, and further change of their classes or subclasses, and a composition such as a peptide for diagnosis of periodontal disease. Another object of the invention lies in providing a vaccine for prophylaxis of periodontal disease containing a peptide having substantially no side-effect other than the desired vaccine action, among these peptides, and an oral cavity composition for prophyl axis or treatment of periodontal disease containing an antibody obtained by immunizing an animal with a peptide thus selected.

SUMMARY OF THE INVENTION

For solving the above problems, the present inventors have made researches into, on various synthetic peptides corresponding to fragments derived from the amino acid sequence of the 41 kD subunit protein constituting the fimbriae of Porphyomonas gingivalis, antigen-antibody reactivity between the synthetic peptides and antibodies against the above protein and biological activities of the synthetic peptides. As a result, they found that peptides corresponding to the amino acid sequence and composed of consecutive 5 to 10 amino acid residues unexpectedly have very excellent characteristics. Namely, although, as mentioned above, synthetic peptides corresponding to fragments derived from the amino acid sequence of the above protein and each having 20 amino acid residues are disclosed in *BBRC.* 130, No. 3, 1335–1341, 1991, the present inventors ascertained that the peptides of the invention are lowered in nonspecific reactivity and therefore, can be used much more safely in various use fields, compared to the above synthetic peptides, and completed the invention.

Thus, according to the invention is provided a peptide corresponding to a fragment derived from the amino acid sequence of the 41 kD subunit protein constituting the fimbriae of Porphyomonas gingivalis, the peptide being characterized in that the fragment is selected from fragments each composed of 5 to 10 consecutive amino acid residues, or a derivative thereof or a salt of the peptide or derivative.

According to a preferred embodiment of the invention, there is provided the above peptide wherein the above fragment is selected from fragments each composed of consecutive at least 5 amino acid residues of the following amino acid sequences (see SEQ ID NOs: 1 to 9 in Sequence listing) or a derivative thereof or a salt of the peptide or derivative.

```
Glu Asn Ala Thr Lys Val Glu Asp Ile Lys  (SEQ ID
                                          NO: 1);

Glu Val Lys Ala Leu Thr Thr Glu Leu Thr  (SEQ ID
                                          NO: 2);

Ala Glu Asn Gln Glu Ala Ala Gly Leu Ile  (SEQ ID
                                          NO: 3);

Ala Ala Gly Leu Ile Met Thr Ala Glu Pro  (SEQ ID
                                          NO: 4);

Thr Gly Ser Leu Thr Thr Phe Asn Gly Ala  (SEQ ID
                                          NO: 5);

Thr Phe Asn Gly Ala Tyr Thr Pro Ala Asn  (SEQ ID
                                          NO: 6);

Gly Phe Tyr Val Leu Glu Asn Asp Tyr Ser  (SEQ ID
                                          NO: 7);

Ala Asn Gly Gly Thr Ile His Pro Thr Ile  (SEQ ID
                                          NO: 8);
``` and

```
Glu Gly Lys Thr Tyr Tyr Pro Val Leu Val  (SEQ ID
                                          NO: 9).
```

According to another embodiment of the invention, there is provided a composition for diagnosis of periodontal disease containing one or a combination of two or more of the peptides or derivatives thereof or salts of the peptides or derivatives.

According to still another embodiment of the invention, there are provided a vaccine for prophylaxis of periodontal disease comprising one or a combination, as its main ingredient, of two or more selected from the peptides or derivatives thereof or salts of the peptides or derivatives, the one or the two or more being characterized in that the peptide is selected from fragments each composed of consecutive at least 5 amino acid residues in the amino acid sequence represented by SEQ ID NO: 1 or 7 in Sequence listing, and pharmaceutically acceptable carriers, and use of the above fragment for preparing such a vaccine, and a treatment method for periodontal disease which comprises a step to administer the vaccine to a mammal.

According to still another embodiment of the invention, there is provided an oral cavity composition for prophylaxis or treatment of periodontal disease containing an antibody obtained by immunizing an animal with one selected from the above peptides or derivatives thereof or salts of the peptides or derivatives, the one being characterized in that the peptide is selected from fragments each composed of consecutive at least 5 amino acid residues in the amino acid sequence represented by SEQ ID NO: 1 or 7 in Sequence listing.

DETAILED DESCRIPTION OF PREFERRED EMBODIMENT(S)

The amino acid sequence of the 41 kD subunit protein constituting the fimbriae of Porphyomonas gingivalis, mentioned in the invention, means the sequence published in D. P. Dickinson et al., *J. Bacteriol.* 170, No. 4, 1658–1665, 1988.

Thus, the peptides of the invention include all peptides so long as they are peptides corresponding to fragments derived from the above amino acid sequence, composed of consecutive 5 to 10 amino acid residues, and fit for the objects of the invention. Among these peptides, those having a region exhibiting high antigenicity when reacted with serum of a patient with periodontal disease are particularly preferred in view of the objects of the invention, and as specific examples thereof, there can be mentioned peptides of various chain lengths having consecutive at least 5 amino acid residues in the amino acid sequences of the above SEQ ID NOs: 1 to 9.

These peptides of various chain lengths can be used as an antigen in the invention because of having 5 amino acid residues at the smallest number, and the above nonspecific reactivity can be lowered by limiting the peptides up to those having 10 amino acid residues at the largest number. Therefore, as specific examples of the peptides of the invention, there can be mentioned peptides composed of consecutive 5, 6, 7, 8, 9 or 10 amino acid residues, in the amino acid sequences of SEQ ID NOs: 1 to 9. For example, as an example of preferred specific peptides among those having 5 amino acid residues, there can be mentioned one represented by the following SEQ ID NO: 10 in Sequence listing:

Glu Asn Ala Thr Lys (SEQ ID NO: 10).

The derivative in the invention means a substance obtained by binding to the peptide protective group(s), functional group(s), a spacer, a carrier or the like. More specifically, as examples of derivatives having a protective group, there can be mentioned a derivative wherein the N-terminus of a peptide of the invention is protected with an acetyl group, an urethane group or the like, and a derivative wherein the C-terminus of a peptide of the invention is protected with an amido group, an ester group or the like. Further, when the peptides are chemically bound, directly or indirectly, to solid phases or carriers, the amino group, carboxyl group or the like of the peptides themselves can be utilized, but for utilizing a phenol group or a sulfhydryl group, a substance obtained by introducing tyrosine or cysteine into a peptide of the invention can also be used, and is also included in the derivative of the invention. Further, when an antibody binds to a peptide of the invention, a spacer can be introduced for the purpose of making the antibody not easily suffer steric hindrance, and a derivative wherein such a spacer is introduced is also included in the derivative. As specific examples of such spacers, there can be mentioned α,ω-diaminoalkanes (n=2–12); α-amino-ω-carboxyalkanes (n=2–10); 3,3'-diaminodipropylamine; succinyl-3,3'-diaminopropylamine; m-aminophenols to which bisdiazobenzidine is bound; Gly-Gly-Gly; Gly-Gly-Tyr; succinyl-1,3-diaminopropan-2-ol; polylysine, etc.

As the derivatives of the invention wherein a carrier is bound, there can be mentioned derivatives wherein lysine used also as the spacer, one of various polymers, bovine serum albumin or the like is bound to a peptide of the invention; derivatives wherein bovine serum albumin, tetanus toxoid, ovalbumin, keyhole limplet hemocyanin, thyroxin binding globulin, γ-globulin, a polysaccharide or the like, which is used when a peptide of the invention is used as an immunogen, is bound to the peptide.

As salts of the peptides or derivatives, when the peptides themselves or their derivatives have a primary, secondary or tertiary amino group, there can be mentioned acid addition salts, for example, salts with an inorganic acid capable of giving a salt therewith such as hydrochloric acid, sulfuric acid, phophoric acid or pyrophophoric acid, salts with an organic acid capable of giving a salt therewith such as acetic acid, lactic acid, palmitic acid, stearic acid, propionic acid, citric acid, tartaric acid, malic acid, ascorbic acid, oxalic acid, methanesulfonic acid, benzenesulfonic acid or p-toluenesulfonic acid. Further, when the peptides themselves or their derivatives have a carboxyl group or a sulfonyl group, there can be mentioned salts, for example, alkali metal salts thereof such as sodium salts and potassium salts, alkaline earth metal salts thereof such as calcium salts and magnesium salts, ammonium salts, triethylamine salts, etc.

Although it is possible to obtain the peptides of the invention by limited decomposition of the 41 kD subunit protein constituting the fimbriae of Porphyomonas gingivalis, it is advantageous to obtain them by a peptide synthesis method known per se. As such peptide synthesis methods, there can, for example, be mentioned chemical synthesis methods [solid phase synthesis method and liquid phase synthesis method (see Jikken Kagaku Koza (Courses of Experimental chemistry) 22, Yuki Gosei (Organic synthesis) IV, pp 258–309, etc., Published on Nov. 30, 1992 by Maruzen Co., Ltd.)] and methods according to genetic engineering.

In this occasion, the synthesis can be conducted using MULTI-PIN PEPTIDE SYNTHESIS KIT (CHIRON MIMOTOPES PTY LTD.: Australia) and a Model 9050 Peptide synthsizer (Millipore corporation).

Derivatives from peptides thus obtained can be obtained by chemical modification means usually used in the technical fields of peptide chemistry. For example, when an aforesaid carrier is chemically bound to such a peptide, a method can be utilized to use glutaraldehtde, a water soluble carbodiimide, succinimide or the like.

For detecting the specific antibody of a patient with periodontal disease, the above peptides or derivatives thereof or salts of the peptides or derivatives can be used alone or in a combination of two or more. As immunological means usable for the detection, known methods can be used, and as examples thereof, there can be mentioned an ELISA method, an RIA method, fluorescent antibody technique, chemical luminescence antibody technique or the like wherein a polystyrene plate, a glass filter, magnetic particles, a latex or the like is used as the solid phase, and the specific antibody of a patient of periodontal disease is detected using a labeled secondary antibody; an immunoagglutination method wherein sheep erythrocytes, a latex or the like is used as the solid phase; immunological nephelometry wherein a latex or the like is used as the solid phase; Western blot technique wherein a nitrocellulose membrane or the like is used as the solid phase; etc. Also as to methods to immobilize a peptide, derivative thereof or salt of the peptide or derivative, as mentioned above, on a solid phase, various known methods can be utilized, and there can, for example, be mentioned a method to physically adsorb it, a method to chemically immobilize it using glutaraldehyde or the like.

Further, immobilization of the antibody of a patient with periodontal disease on a solid phase can be conducted using an anti-human antibody or by physical adsorption, and after the immobilization, various immunological methods using a labeled peptide can be utilized.

When a peptide of the invention is used as a vaccine for prophylaxis of periodontal disease, it can also be adsorbed on a carrier protein such as, bovine serum albumin, tetanus toxoid or the like. In addition, the peptide can be orally administered or parenterally, topically administered together with an adjuvant such as aluminum hydroxide, alum or muramyl dipeptide which is a synthetic adjuvant. It is possible to conduct the parenteral, topical administration, for example, through subcutaneous, intracutaneous, intramuscular or intravenous administration, but since as to periodontal disease, immune response at the limited site of the local gingiva is known, administration into the gingiva can also be adopted. As to the adjuvant, it is desirable to add aluminum hydroxide gel so that its final concentration can be 0.05 to 0.2 mg/ml. It is suitable that the content of the peptide in the vaccine to be administered at a time is 0.004 to 2.5 mg, preferably 0.02 to 0.6 mg. It is preferred to add 0.01% (w/v) of thimerosal as an antiseptic.

Further, apart from directly using the peptide as a vaccine, it is also possible to use, for prophylaxis or treatment of periodontal disease, an oral cavity composition containing a specific antibody found in the serum, cow's milk or eggs obtained after an ox, chicken or the like is immunized with the peptide.

As for a method of immunizing a mammal with a peptide of the invention, as usually conducted, for example, a complex obtained by binding the peptide to a carrier such as bovine serum albumin or tetanus toxoid can be administered together with an adjuvant such as Freund's complete adjuvant or aluminum hydroxide to a living body.

As mammals to be immunized, there can be used goat, sheep, horse, cattle, etc. When antiserum or milk containing a specific antibody obtained by immunizing a mammal with a complex of the peptide with the carrier is used, several kinds of antisera or milks containing a specific antibody can be mixed.

As to preparation of an antibody against the peptide through hen's eggs, for example, a specific antibody can be prepared by immunizing a chicken once or twice with a complex obtained by binding the peptide to a carrier such as bovine serum albumin or tetanus toxoid, together with an adjuvant such as Freund's complete adjuvant or aluminum hydroxide, collecting, from one to two months later, eggs, separating yolk, adding phosphate-buffered physiological saline and chloroform to the yolk, stirring the mixture, and separating the water soluble part as the upper layer which contains the specific antibody.

An antibody against the peptide, prepared by the invention, can be compounded into emulsions, dispersions, pastes, gels or aerosols. Specifically, the antibody can be compounded into substances such as toothpastes, chewing gums, mouthwashes or gargles.

Further, the peptides of the invention can be used for preparing a specific antibody, and the resultant specific antibody can be utilized for diagnosis of periodontal disease, or for passive immunity as a prophylactic means against infection with Porphyomonas gingivalis.

Still further, the peptides of the invention can be used for producing polyclonal antibodies or monoclonal antibodies. For obtaining polyclonal antibodies, either of large and small animals usually used can be used. After a host animal is immunized with such a peptide, an antibody can be recovered by a known method. On the other hand, a monoclonal antibody can be obtained by immunizing a mouse with the peptide, and fusing a B-lymphocyte thereof and a myeloma cell.

The invention is specifically described below by examples, but it should not be construed that the invention claimed in the attached CLAIM is limited thereby.

EXAMPLE 1

Synthesis of Partial Peptides Using Multi Pin Peptide Synthesis Kit

Peptides composed of 10 amino acid residues were synthesized, based on the estimated amino acid sequence of the fimbriae of Porphyomonas gingivalis strain 381 determined by D. P. Dickinson et al. (*J. Bacteriol.* 170, No. 4, 1658–1665, 1988), at intervals of 5 amino acid residues from the N-terminus side, using MULTI-PIN PEPTIDE SYNTHESIS KIT (Non-Cleavable Type: Code No. 593–28201) made by CHIRON MIMOTOPES PTY LTD (Australia).

First, the tip of the pin was immersed in dimethylformamide (DMF) for 2 minutes, and washed by shaking three times in methanol (MeOH) for 10 minutes. The tip was air dried for 30 minutes, and then immersed in 20% piperidine/DMF for 30 minutes to conduct deprotection. Then, the tip was immersed in DMF for 10 minutes, and washed by shaking 4 times in methanol (MeOH) for 2 minutes. The tip was air dried for 30 minutes, immersed in DMF for 5 minutes, and then immersed in each Fmoc-amino acid solution (60 mM)/DMF+120 mM 1-hydroxybenzotriazole monohydrate (HoBt), and reaction was conducted at room temperature for 16 hours to couple the tip and the desired amino acid. From the next day, the coupling operations were repeated in the same manner as above, using the next amino acid.

When the coupling up to the desired 10 amino acid residues was completed, the tip was immersed in DMF for 2 minutes to swell it, and then washed by shaking it three times in MeOH for 10 minutes. After air drying for 30 minutes, the tip was immersed in 20% piperidine/DMF for 30 minutes to conduct deprotection. Then, the tip was immersed in DMF for 10 minutes, and washed by shaking it 4 times in MeOH for 2 minutes. After air drying for 30 minutes, the tip was immersed in a mixed liquid of DMF:acetic anhydride:triethylamine=50:5:1 for 90 minutes to conduct acetylation, and the tip was washed by shaking it in MeOH for 2 minutes. After air drying for 15 minutes, the tip was immersed in a mixed liquid of trifluoroacetic acid:ethanedithiol:thioanisole=95:2.5:2.5 for 60 minutes to conduct deprotection. The tip was air dried for 10 minutes, subjected to ultrasonic cleaning for 15 minutes, and further air dried for 10 minutes.

Test Example 1

Elucidation of the Epitope Using Serum of a Patient of Periodontal Disease

Elucidation of the epitope was conducted by an ELISA method, using the peptides synthesized in Example 1 and serum of a patient with periodontal disease.

First, the tip of the pin to which the peptide is bound was blocked by immersing in 2% bovine serum albumin (BSA)/phosphate-buffered physiological saline+Tween 20 (PBST) at room temperature for one hour, and then washed by shaking it three times in PBST for 5 minutes. Then, serum of a normal subject or the patient, on which addition of the fimbriae of Porphyomonas gingivalis and absorption operation were conducted or not conducted, were prepared as primary antibodies. Each of the serum was diluted $10^5$ times with 0.1% casein/PBST, and reacted with the peptide bound to the tip at 4° C. for 16 hours. The tip was washed by shaking it three times in PBST for 5 minutes, and then alkaline phosphatase-labeled anti-human IgG antibody (diluted $10^3$ times)/0.1% casein/PBST as a secondary antibody was reacted therewith. The tip was washed by shaking three times in PBST for 5 minutes, and subjected to reaction in p-nitrophenyl phosphate/diethanolamine buffer at 37° C. for 3 hours, and absorbance (405 nm) was measured. Peptides having a difference in absorbance between before and after the absorption operations of 0.2 or more were selected. Each of these peptides was subjected to ultrasonic cleaning in 0.1 M phosphate buffer (pH 7.2)+1% SDS+0.1% 2-mercaptoethanol (55–65° C.), washed twice in distilled water (60° C.) for 30 seconds, and further washed by shaking for 30 minutes. Then, the peptide was boiled in methanol for 15 seconds, air dried for 15 minutes, and then provided for a next ELISA method.

As a result, peculiar epitopes reacting with the serum of the patient were found out. The results are shown in Table 1.

TABLE 1

Particular peptides reacting with the serum of a patient with periodontal disease

| Amino acid sequence | Abbreviation |
|---|---|
| Glu Asn Ala Thr Lys Val Glu Asp Ile Lys: | Peptide 1 |
| Glu Val Lys Ala Leu Thr Thr Glu Leu Thr: | Peptide 2 |
| Ala Glu Asn Gln Glu Ala Ala Gly Leu Ile: | Peptide 3 |
| Ala Ala Gly Leu Ile Met Thr Ala Glu Pro: | Peptide 4 |
| Thr Gly Ser Leu Thr Thr Phe Asn Gly Ala: | Peptide 5 |
| Thr Phe Asn Gly Ala Tyr Thr Pro Ala Asn: | Peptide 6 |
| Gly Phe Tyr Val Leu Glu Asn Asp Tyr Ser: | Peptide 7 |
| Ala Asn Gly Gly Thr Ile His Pro Thr Ile: | Peptide 8 |
| Glu Gly Lys Thr Tyr Tyr Pro Val Leu Val: | Peptide 9 |

EXAMPLE 2

Synthesis of Peptides Using a Peptide Synthesizer

Each of the particular epitopes reacting with the serum of the patient of periodontal disease, found out in Test example 1, was synthesized according to R. B. Merrifield (*J. Am. Chem. Soc.* 85, 2149–2154, 1963) using a model 9050 peptide synthesizer (Millipore corporation). Purification was conducted by reverse-phase HPLC using Capcell Pak C18 SG 120 (1.5×1.5 cm: Shiseido) column and an acetonitrile concentration gradient of 6 to 60%, and thereby, the peptide fraction was recovered as the main peak. As to each peptide thus prepared and purified, its composition was ascertained by quantitative amino acid analysis, and its amino acid sequence by automated Edman degradation using a model 6400/6600 protein sequencer (Japan Millipore corporation).

Test Example 2

Assay of the Specific Antibody in Serum of a Patient with Periodontal Disease Using the Peptides One mg of each peptide synthesized in Example 2 was dissolved in 1 ml of 0.1 M phosphate buffered saline (PBS, pH 6.0), 5 mg of sulfated SMCC (made by Pierce Co.) was added, and the mixture was incubated at 30° C. for 30 minutes to conduct maleimidization, and then subjected to Sephadex G-10 column chromatography, and the first eluate fraction was collected. 7 mg of bovine serum albumin (BSA: made by Wako Pure Chemical Industries, Ltd.) was dissolved in 1 ml of 0.1 M phosphate buffer (pH 6.0), 10 mM EDTA, the solution was mixed with the above maleimidized peptide, and the mixture was subjected to reaction at 30° C.

for 1 hour. The resultant peptide-modified BSA was subjected to Sephadex G-50 column chromatography, and the first eluate fraction was collected as a plate-preparing antigen solution.

Then, six kind of peptides were synthesized after the process of Example 2, and a plate-preparing antigen solution was similarly prepared as a control.

Each of the resultant antigen solutions was diluted with 0.1 M carbonate buffer (pH 9.6), 150 mM NaCl to give 100 ml of a solution. 10 μl/well of the solution was put in a polystyrene-made microtiter plate (Immunoplate II; maxisorp type; made by Nunc Co.) and left alone at 4° C. overnight, and washing was conducted three times each with 200 μl/well of PBS, using a microtiter automatic washer (hereafter abbreviated as washer; made by Bio-Rad Laboratories). 250 μl/well of PBS containing 0.1% gelatin (made by Nitta Gelatin Co., Ltd.) was added and the mixture was allowed to stand at 4° C. overnight to block the plate. The blocking solution was removed by absorption, and the plate was dried by a vacuum dryer, put in an aluminum bag, and after sealing the bag, kept at 4° C. for the following assay.

Sera of patients of periodontal disease (n=3) and normal subjects (n=3) were used as samples, and each serum was diluted 100 times with PBS containing 10% bovine serum. 100 μl portions of these dilutions were added to the plates coated with various antigens, respectively, and incubation was conducted at 37° C. for 1 hour. Each plate was washed three times with 200 μl of PBST using the washer, 100 μl of a commercially available peroxidase-labeled human IgG antibody (diluted $10^3$ times)/0.1% Casein/PBST was added as a secondary antibody, and incubation was conducted again at 37° C. for 1 hour. The plate was washed in the same manner as above, 100 μl of an o-phenylenediamine solution was added, incubation was conducted at 37° C. for 30 minutes, 100 μl of 0.1 N sulfuric acid was added to stop the reaction, and then, absorbance (405 nm) was measured by a microplate reader (made by Bio-Rad Laboratories) using the reaction well of no addition of the specimen as a control. The results of assay using the various antigen plates are shown in Table 2. The measures values are average absorbances of 3 specimens each of the patient group of periodontal disease and the normal subject group.

On the peptides having the amino acid sequences shown in Table 1 among the used peptides, specific reactivity was observed in the patient group of periodontal disease. Therefore, it was revealed that by using these peptides as antigens, it is possible to detect anti-Porphyomonas gingivalis fimbria antibodies contained in sera of patients with periodontal disease, and these peptides are useful for screening of cases with periodontal disease.

TABLE 2

Assay of antibody titers of the sera of the periodontal disease patient group and normal subject group using plates coated with various peptides

| Peptides applied | Patient group with peridontal disease | Normal subject group |
| --- | --- | --- |
| Peptide of the invention | | |
| Peptide 1 | 1.016 | 0.145 |
| Peptide 2 | 0.566 | 0.205 |
| Peptide 3 | 0.623 | 0.214 |
| Peptide 4 | 0.941 | 0.197 |
| Peptide 5 | 0.760 | 0.165 |
| Peptide 6 | 0.675 | 0.141 |
| Peptide 7 | 1.224 | 0.226 |
| Peptide 8 | 0.935 | 0.182 |
| Peptide 9 | 0.546 | 0.186 |
| Comparative peptide | | |
| Val Met Val Tyr Asn Gly Glu Gln Gln Glu | 0.165 | 0.172 (SEQ ID NO: 11) |
| Arg Thr Leu Val Val Met Ala Asn Thr Gly | 0.199 | 0.161 (SEQ ID NO: 12) |
| Asn His Ile Glu Asn Asp Pro Leu Lys Ile | 0.205 | 0.201 (SEQ ID NO: 13) |
| Asp Ala Asn Tyr Leu Thr Gly Ser Leu Thr | 0.196 | 0.145 (SEQ ID NO: 14) |
| Trp Leu Ser Arg Asn Tyr Val Ala Pro Ala | 0.210 | 0.204 (SEQ ID NO: 15) |
| Leu Cys Val Tyr Gly Lys Leu Gln Lys Asn | 0.182 | 0.213 (SEQ ID NO: 16) |

Test Example 3

Inhibitory Test of Porphyomonas Gingivalis Infection Using the Peptides

Each peptide synthesized in Example 2 was administered together with FIA (Freund's incomplete adjuvant) or FCA (Freund's complete adjuvant), as a water-in-oil type emulsifier, into the sole of the right hind leg of a guinea pig in an amount of 500 μg/animal/time. Thereafter, on the 28th day, 200 μl of a suspension of $10^{11}$ cells/ml of the bacterium was intracutaneously inoculated into the right flank of the same guinea pig after the hair at the region was shaved. 24 hours later, the longest length and shortest length of the resultant red coloring were measured, and the product of them was calculated. From the product was calculated the inhibition rate. These results are shown in Table 3, and as seen therefrom, particularly, Peptide 1 and Peptide 7 exhibited strong inhibitory effect against infection with Porphyomonas gingivalis.

TABLE 3

Inhibitory effect against infection with *Porphyromonas gingivalis* using peptides

| Test group | Longest length × shortest length*) (mm²) | Inhibition rate (%) |
|---|---|---|
| FIA[a)] | 1947 | 0 |
| FCA[b)] | 1784 | 8.3 |
| *Porphyromonas gingivalis* fimbriae + FIA | 1571 | 19.3 |
| *Porphyromonas gingivalis* fimbriae + FCA | 1486 | 23.7 |
| Peptide 1 + FCA | 660 | 66.1 |
| Peptide 2 + FCA | 1179 | 39.5 |
| Peptide 3 + FCA | 1155 | 40.7 |
| Peptide 4 + FCA | 851 | 56.3 |
| Peptide 5 + FCA | 1063 | 45.4 |
| Peptide 6 + FCA | 1112 | 42.9 |
| Peptide 7 + FCA | 240 | 87.7 |
| Peptide 8 + FCA | 1022 | 47.5 |
| Peptide 9 + FCA | 1265 | 35.0 |

[a)]FIA: Freund's incomplete adjuvant
[b)]FCA: Freund's complete adjuvant

TABLE 3-continued

Inhibitory effect against infection with *Porphyromonas gingivalis* using peptides

| Test group | Longest length × shortest length*) (mm²) | Inhibition rate (%) |
|---|---|---|

*) Inhibition (%) = $\dfrac{A - B}{A} \times 100$

A: Longest length × shortest length in the FIA inoculation group
B: Longest length × shortest length in the peptide inoculation group in the invention

Test Example 4

Test on Immunization of Mice with the Peptides

Each peptide synthesized in Example 2 was dissolved in PBS so as to make the concentration 200 μg/ml, the solution was mixed with the same volume of FCA, and the mixture after emulsification was subcutaneously injected into mice at the back (3 animals per group). 4 weeks later, the antibody titer in the serum or saliva against the peptide was assayed by an ELISA method.

The fimbrial protein of Porphyomonas gingivalis was adsorbed on each well of a 96-well microtiter plate for ELISA, and a dilution of the serum with PBS ($1/10^5$), a dilution of the saliva with PBS (1/500), or a solution obtained by adding each peptide or the fimbrial protein of Porphyomonas gingivalis is to the dilution of the serum or saliva to cause absorption was put in the well. Reaction was conducted at 37° C. for 1 hour, and then assay was conducted by a usual ELISA method.

The results are shown in Table 4. As apparent therefrom, when the serum or saliva was subjected to absorption operations with each peptide, decrease of absorbance was observed. From the above results, it was ascertained that an antibody against each peptide or the fimbrial protein was produced in the serum and saliva of the mice immunized with each peptide.

TABLE 4

Immunization test with peptides

| | | Antibody titer before and after absorption operation[c)] | | | |
|---|---|---|---|---|---|
| | | Serum ($1/10^5$) | | Saliva (1/500) | |
| Test group | Body weight (Average g) | Before absorption | After absorption | Before absorption | After absorption |
| Fimbrial protein + FCA[d)] | 25 | 1.10 | 0.14 | 1.22 | 0.19 |
| Control | 27 | 0.08 | 0.07 | 0.18 | 0.16 |
| Peptide 1 + FCA | 25 | 0.62 | 0.19 | 0.61 | 0.11 |
| Peptide 2 + FCA | 26 | 0.34 | 0.15 | 0.36 | 0.17 |
| Peptide 3 + FCA | 26 | 0.38 | 0.16 | 0.37 | 0.09 |
| Peptide 4 + FCA | 27 | 0.52 | 0.13 | 0.49 | 0.12 |
| Peptide 5 + FCA | 28 | 0.45 | 0.11 | 0.42 | 0.15 |
| Peptide 6 + FCA | 26 | 0.41 | 0.12 | 0.39 | 0.11 |
| Peptide 7 + FCA | 23 | 0.67 | 0.14 | 0.69 | 0.15 |
| Peptide 8 + FCA | 25 | 0.49 | 0.11 | 0.45 | 0.14 |
| Peptide 9 + FCA | 26 | 0.32 | 0.13 | 0.34 | 0.13 |

[c)] Antibody titer: $A_{405}$ value by the ELISA method at each dilution rate
[d)] FCA: Freund's complete adjuvant

Test Example 5

Investigation of Various Immunobiological Activities Using the Peptides

On 9 peptides shown in Test example 1, Test example 2, Test example 3 and Test example 4, mitogen activity, polyclonal B-cell activation, abilities to induce production of inflammatory cytokines such as TNF-alpha and IL-6 and hemagglutinating activity were assayed as biological activities. Assay methods of various biological activities are shown below.

Mitogenic Activity

Spleen cells of BALB/c mice were cultured together with each of the nine peptides obtained in Example 2 for 48 hours, and $^3$H-thymidine was added 6 hours before the final culture. After completion of the culture, uptake of ³H-thymidine by the cells was measured using a scintillation counter to examine the mitogen activity of each peptide.

Polyclonal B-Cell Activation

Spleen cells of BALB/c mice were cultured together with each of the nine peptides obtained in Example 2 for 72 hours, and the number of antibody-producing cells in the spleen cells was measured by an ELISPOT method to examine the polyclonal B-cell activation of each peptide.

Inductive Ability of TNF-alpha Production

Macrophages in human peripheral blood were cultured together with each of the nine peptides obtained in Example 2 for 24 hours. After completion of the culture, the culture supernatant was added to L929 cells for further 24 hours, and then the number of L929 dead cells was measured to examine inductive ability the TNF-alpha production by each peptide.

Inductive Ability of IL-6 Production

Macrophages in human peripheral blood were cultured together with each of the nine peptides obtained in Example 2 for 24 hours. Then, the amount of IL-6 in the culture supernatant was assayed by an ELISA method to examine the inductive ability of IL-6 production by each peptide.

Hemagglutinating Activity 0.1 ml portions of each of solutions of a peptide 2-fold serially diluted in PBS were put in each well of a 96-well round-bottomed microtitration plate, and 0.1 ml portions of a suspension of 2% rabbit erythrocytes were added, respectively. After culture at 37° C. for 2 hours, the hemagglutinating pattern of each well was estimated.

The results of the above tests are shown in Table 5, and as apparent therefrom, Peptide 1 and Peptide 7 do not exhibited any of these activities.

From these results, Peptide 1 and Peptide 7 not having any of the various immunobiological activities were decided to be used as a vaccine for prophylaxis of periodontal disease.

TABLE 5

Various immunobiological activities of peptides

| | Mitogenic activity | Polyclonal B-cell activation | TNF-alpha production | IL-6 production | Hemagglutinating activity |
|---|---|---|---|---|---|
| Peptide 1 | − | − | − | − | − |
| Peptide 2 | + | + | + | + | ± |
| Peptide 3 | − | − | + | + | ± |
| Peptide 4 | − | − | + | + | − |
| Peptide 5 | N.D.e) | N.D. | N.D. | N.D. | + |
| Peptide 6 | N.D. | N.D. | N.D. | N.D. | + |
| Peptide 7 | − | − | − | − | − |
| Peptide 8 | N.D. | N.D. | N.D. | N.D. | ± |
| Peptide 9 | N.D. | N.D. | N.D. | N.D. | ± | e) N.D.: Not tested

EXAMPLE 3

Preparation of a Vaccine

Peptide 1 or Peptide 7 among the peptides prepared in Example 2 was dissolved in 0.75 M phosphate-buffered physiological saline so that the concentration of the peptide could be 1.0 mg/ml, aluminum hydroxide gel was added as an adjuvant so that the concentration could be 0.2 mg/ml, and 0.01% (w/v) of thimerosal was added to give a vaccine.

Test Example 6

Inhibitory Test of Porphyomonas gingivalis Infection

The effects of vaccine on Peptide 1 and Peptide 7 selected from the results of Test example 1, Test example 2, Test example 3, Test example 4 and Test example 5 were examined according to the following method using degree of resorption of alveolar bone and antibody titer as measures, using the vaccine described in Example 3.

3-week-old Golden hamsters (one group consisting of 6 animals, 5 groups in total, ① Porphyomonas gingivalis strain 381 fimbria immunity induction group, ② Peptide 1 immunity induction group, ③ Peptide 7 immunity induction group, ④ Nonimmunity induction group, ⑤ Nonimmunity noninduction group) were used.

Each of the vaccines of the invention was subcutaneously administered at the oral cavity in amounts of 0.2 ml portions on the third week and the fourth week after the birth, and 0.4 ml on the fifth week.

Induction of periodontal disease was conducted by culturing Porphyomonas gingivalis strain 381 in GAM broth at 37° C. for 20 hours, collecting the cells by centrifugation, suspending the cells in phisiological saline so that the cell concentration could be $10^9$ cells/ml, administering 0.2 ml portions of the suspension into the oral cavity of the Golden hamsters for 7 days starting from the sixth week after the birth, and thereafter, administering the suspension once a week.

After the start of the cell administration, the animals were allowed to freely ingest Diet 2000 (made by Funabashi Nojo) as a dental caries-inducing feed and water.

After the Golden hamsters were fed for 80 days, 1 ml/kg portions of 0.5% pilocarpine hydrochloride were intraperitoneally administered, and saliva was taken from them. Thereafter, blood was taken from the abdominal aorta of each animal, and serum was obtained therefrom. Further, a bone preparation from each hamster was produced by amputating the head, heat treating the head using an autoclave, removing the muscle part, and washing with water and drying the remaining matter.

The saliva and serum were assayed for antibody titer against the peptide.

The bone preparation was assayed for degree of resorption of the alveolar bone of a molar according to the method$^f$) of Tsukiyama et al. (*Koku Eisei Kaishi* (Jornal of Hygiene of Oral Cavity) 28, No. 3, 149, 1978).

f) The bone preparation was stained with 20% silver nitrate solution for 5 minutes, and after water washing and drying, the distance from the enamel-cement junction to the alveolar bone edge was measured by a stereoscopic microscope (magnification 15-fold).

In the inhibitory test of Porphyomonas gingivalis infection, as seen in Table 6, strong resorption of the alveolar bone was observed in the nonimmunity induction group, but in the immunity induction groups, the degree of resorption of the alveolar bone was inhibited in almost the same degree as in the nonimmunity noninduction group.

As to antibody titers in the sera and saliva of the test groups against the peptides, the antibody titers were significantly incresed in the peptide administration groups, but the antibody titer in the nonimmunity induction group was almost equal to that in the nonimmunity noninduction group.

These results are shown in Table 6, and as seen therefrom, in Peptide 1 and Peptide 7 were observed inhibition of absoption of the alveolar bone, and increse of antibody titer in the sara and saliva.

the suspension (550 nm) was adjusted so as to be 0.5. 100 µl portions of the cell suspension and 100 µl portions of dilutions of each antibody solution obtained in Example 4 were adequately mixed, respectively, and the mixtures were put in a 96-well round-bottomed microtitration plate and subjected to reaction at 4° C. for 16 hours, respectively, to conduct cell agglutination test. The results are shown in Table 7.

TABLE 6

Inhibitory test of *Porphyromonas gingivalis* infection in Golden hamster

| Test group | Body weight (at the time of production of bone preparation (average g) | Absorbance of alveolar bone (average) | Antibody titer[g] Serum ($1/10^5$) | Antibody titer[g] Saliva (1/500) |
|---|---|---|---|---|
| Fimbria immunity induction group | 128 | 52 | 1.08 | 1.29 |
| Peptide 1 immunity induction group | 124 | 48 | 0.65 | 0.62 |
| Peptide 7 immunity induction group | 123 | 41 | 0.71 | 0.79 |
| Nonimmunity induction group | 116 | 97 | 0.10 | 0.21 |
| Nonimmunity noninduction group | 135 | 34 | 0.06 | 0.16 |

[g]Antibody titer: $A_{405}$ value by the ELISA method at each dilution rate

Test Example 7

Safety of the Vaccine for Prophylaxis of Periodontal Disease

The vaccines obtained in Example 3 were tested by the staining test, aseptic test and acute toxicity test (mice) according to the A Test Methods in Biological Preparation Standards notified by the Ministry of Welfare, but abnormality to be specially mentioned was not recognized in any of the tests.

EXAMPLE 4

Obtention of Murine Antisera Against the Peptides

BALB/c mice were immunized with 300 µg portions of each of the peptides whose effects were ascertained in Test example 3, together with FCA, respectively, to give antisera against the respective peptides. In the same manner as above, antisera against the whole cell of Porphyomonas gingivalis (100 µg/time) and the fimbria (100 µg/time) were obtained, respectively.

The respective antisera against the peptides, whole cell and fimbria were purified through ammonium salfate fractionation and ion exchange chromatography, and antibody solutions each having a protein content of 1 mg/ml were prepared.

Test Example 8

Cell Agglutination Test Using Antibodies Against the Peptides

Porphyomonas gingivalis was inoculated in a medium comprising GAM broth, Brain-Heart Infusion broth or the like having added thereto hemin and menadione and cultured under an anaerobic condition at 37° C. for 20 hours, the cells were collected and suspended in phosphate-buffered physiological saline, and the degree of resorption of

TABLE 7

Cell agglutination test

| | Dilution rate of antibody | | | | | |
|---|---|---|---|---|---|---|
| | $10^{-1}$ | $10^{-2}$ | $10^{-3}$ | $10^{-4}$ | $10^{-5}$ | $10^{-6}$ |
| Anti-entire cell antiserum | +++ | +++ | +++ | ++ | + | − |
| Anti-fimbria serum | +++ | +++ | ++ | + | − | − |
| Anti-Peptide 1 serum | +++ | +++ | ++ | − | − | − |
| Anti-Peptide 7 serum | +++ | +++ | ++ | − | − | − |

EXAMPLE 5

| Preparation of toothpaste | |
|---|---|
| Calcium secondary phosphate dihydride | 45% |
| Glycerol | 15% |
| Sorbitol | 10% |
| Carboxymethyl cellulose | 5% |
| Sodium lauryl sulfate | 3% |
| Saccharin | 0.1% |
| Water | 21.9% |
| | 100% |

0.01% of the antibody solution against Peptide 1 obtained in Example 4 is incorporated into the above components.

EXAMPLE 6

| Preparation of mouthwash | |
|---|---|
| Ethanol | 22% |
| Saccharin | 0.1% |
| Lauryldiethanolamine | 0.3% |
| Flavor | 1% |

| -continued |  |
|---|---|
| Preparation of mouthwash | |
| Water | 76.6% |
|  | 100% |

0.01% of the antibody solution against Peptide 7 obtained in Example 4 is incorporated into the above components.

Test Example 9

Passive Immunity Test Using Antibodies Against the Peptides

Effect of passive immunity on Golden hamsters was examined by rinsing the mouth and brushing the teeth using the antibody solutions against the peptides obtained in Example 4.

Effect of passive immunity by the invention was examined according to the following method using degree of resorption of the alveolar bone and antibody titer as measures. 3-week-old Golden hamsters (one group 6 animals, 4 groups, ①Anti-Peptide 1 antibody administration induction group, ②Anti-Peptide 7 antibody administration induction group, ③Nonpassive immunity induction group, ④Nonpassive immunity noninduction group) were used.

Induction of periodontal infection was conducted by culturing Porphyomonas gingivalis strain 381 in GAM broth at 37° C. for 20 hours, collecting the cells by centrifugation, suspending the cells in phisiological saline so that the cell concentration could be $10^9$ cells/ml, administering 0.2 ml portions of the suspension into the oral cavity of the Golden hamsters wherein the first molar of the lower jaw was ligated with cotton thread.

After the start of the cell administration, the animals were allowed to freely ingest Diet 2000 (made by Funabashi Nojo) as a dental caries-inducing feed and water.

From the next day of the cell administration, rinse of the mouth and the brushing were conducted every day using the oral cavity composition containing the antibody against the peptide, obtained in Example 5.

A bone preparation from each hamster was produced by amputating the head, heat treating the head using an autoclave, removing the muscle part, and washing with water and drying the remaining matter.

As to infection protection effect by passive immunity, as shown in Table 8, strong degree of resorption of the alveolar bone was observed in the nonpassive immunity induction group, but in the anti-Peptide 1 antibody administration induction group and the anti-Peptide 7 antibody administration induction group, degree of resorption of the alveolar bone was inhibited to almost the same degree as in the nonpassive immunity noninduction group.

TABLE 8

Passive immunity test using Golden hamsters

| Test group | Body weight at the time of production of bone preparation (average g) | | Absorbance of alveolar bone (average) | |
|---|---|---|---|---|
|  | Mouth rince | Brushing | Mouth rince | Brush |
| Anti-Peptide 1 antibody adminstration induction group | 120 | 122 | 60 | 51 |
| Anti-Peptide 7 antibody administration induction group | 120 | 123 | 56 | 46 |
| Nonpassive immunity inductioin group | 118 | 116 | 98 | 97 |
| Nonpassive immunity noninduction group | 122 | 124 | 41 | 39 |

Industrial Applicability

According to the invention, by synthesizing peptides of the 41 kD subunit protein constituting the fimbriae of Porphyomonas gingivalis, and utilizing the peptides as a antigen, it is possible to accurately assay specific antibodies in the sera, saliva and gingival crevice fluid of patients with periodontal disease, and further their classes or subclasses.

Further, when a peptide of the 41 kD subunit protein constituting the fimbriae of Porphyomonas gingivalis is synthesized, and the peptide is administered together with a suitable immunopotentiating agent into the gingiva, a specific antibody is effectively increased and infection with Porphyomonas gingivalis is inhibited. Further, it is also possible to use an oral cavity composition containing an antibodies contained in serum, milk or egg obtained by immunizing an ox, chicken or the like with such a peptide, for prophylaxis or treatment of periodontal disease.

Thus, the present invention can be utilized in the manufacturing industry of diagnostic reagents, the manufacturing industry of vaccines, etc.

What is claimed is:

1. An isolated peptide consisting of 5 or 10 successive amino acid residues in the amino acid sequence of SEQ ID No. 1, 2, 3, 4, 5, 6, 7, 8 or 9, or a salt of the isolated peptide, said isolated peptide having specific reactivity with serum of a periodontal disease patient.

2. A composition comprising one or more isolated peptide (s) or salt(s) thereof, wherein each peptide consists of 5 or 10 successive amino acid residues in the amino acid sequence of SEQ ID NO: 1, 2, 3, 4, 5, 6, 7, 8 or 9, said isolated peptide(s) or salt(s) thereof having specific reactivity with serum of a periodontal disease patient.

3. The composition according to claim 2, which is for the diagnosis of periodontal disease.

4. A vaccine comprising one or more isolated peptide(s) or salt(s) thereof, and one or more pharmaceutically acceptable carriers, said isolated peptide consisting of 5 or 10 successive amino acid residues in the amino acid sequence of SEQ ID No. 1 or 7 and having specific reactivity with serum of a periodontal disease patient.

5. The vaccine according to claim 4, which is for the prophylaxis of periodontal disease.

6. The vaccine according to claim 5, which is for administration into gingiva.

7. An oral cavity composition for prophylaxis or treatment of periodontal disease comprising an antibody obtained by immunizing an animal with one or more isolated peptide(s) or salt(s) thereof, each of said isolated peptide consisting of 5 or 10 successive amino acid residues in the amino acid sequence of SEQ ID No. 1 or 7 and having specific reactivity with serum of a periodontal disease patient.

8. A method for protecting a mammal from periodontal disease or for treating a mammal suffering from periodontal disease, which comprises administering the vaccine according to claim 4 to the mammal.

9. The isolated peptide or salt thereof according to claim 1, wherein the peptide consists of the amino acid sequence as set forth in SEQ ID No. 1, 2, 3, 4, 5, 6, 7, 8 or 9.

10. The vaccine according to claim 4, wherein at least one of the isolated peptide consists of the amino acid sequence as set forth in SEQ ID No. 1 or 7.

11. The oral cavity composition according to claim 7, wherein at least one of the isolated peptide consists of the amino acid sequence as set forth in SEQ ID No. 1 or 7.

12. The method according to claim 8, wherein at least one of the isolated peptide consists of the amino acid sequence as set forth in SEQ ID No. 1 or 7.

13. An isolated peptide consisting of the amino acid sequence as set forth in SEQ ID No. 10 or a salt of the isolated peptide, said isolated peptide having a specific reactivity with serum of a periodontal disease patient.

* * * * *